US012575799B2

(12) United States Patent
Wendlandt et al.

(10) Patent No.: US 12,575,799 B2
(45) Date of Patent: Mar. 17, 2026

(54) RADIOGRAPHIC DETECTOR

(71) Applicant: CARESTREAM HEALTH, INC.,
Rochester, NY (US)

(72) Inventors: William C. Wendlandt, Rush, NY
(US); Anthony Dirisio, Rochester, NY
(US); Evan P. Carmichael, Rochester,
NY (US); Todd D. Bogumil, Rochester,
NY (US); Steven R. Lippold, Bergen,
NY (US)

(73) Assignee: Carestream Health, Inc., Rochester,
NY (US)

( * ) Notice: Subject to any disclaimer, the term of this
patent is extended or adjusted under 35
U.S.C. 154(b) by 227 days.

(21) Appl. No.: 18/635,121

(22) Filed: Apr. 15, 2024

(65) Prior Publication Data

US 2024/0277307 A1      Aug. 22, 2024

Related U.S. Application Data

(63) Continuation-in-part of application No. 17/627,705,
filed as application No. PCT/US2020/045592 on Aug.
10, 2020, now Pat. No. 11,988,786.

(60) Provisional application No. 62/885,423, filed on Aug.
12, 2019.

(51) Int. Cl.
A61B 6/00 (2024.01)
A61B 6/42 (2024.01)

(52) U.S. Cl.
CPC ................................. A61B 6/4283 (2013.01)

(58) Field of Classification Search
CPC ................................................... A61B 6/4283
See application file for complete search history.

(56) References Cited

U.S. PATENT DOCUMENTS

| | | | |
|---|---|---|---|
| 5,843,131 A | 12/1998 | McDonough | |
| 7,046,764 B1 * | 5/2006 | Kump ................. | A61B 6/4283 |
| | | | 378/117 |
| 7,317,190 B2 | 1/2008 | Ertel et al. | |
| 7,488,946 B2 | 2/2009 | Hennessy et al. | |
| 7,495,227 B2 | 2/2009 | Hennessy et al. | |
| 7,566,877 B2 | 7/2009 | Bhatt | |
| 7,663,114 B2 | 2/2010 | Aoyagi | |
| 7,742,274 B2 | 6/2010 | Utschig | |
| 7,755,053 B2 | 7/2010 | Chiyoma | |
| 7,800,065 B2 | 9/2010 | Konkle et al. | |
| 8,035,084 B2 | 10/2011 | Sumi | |
| 8,269,182 B2 | 9/2012 | Konkle et al. | |

(Continued)

FOREIGN PATENT DOCUMENTS

| | | |
|---|---|---|
| EP | 0 546 211 B2 | 9/1998 |
| JP | 2013-33055 A | 2/2013 |

(Continued)

OTHER PUBLICATIONS

International Search Report for International Patent Application
PCT/US2020/045592, mailed on Oct. 8, 2020, 3 pages.

*Primary Examiner* — Mark R Gaworecki
(74) *Attorney, Agent, or Firm* — Eugene I Shkurko

(57) ABSTRACT

A digital radiographic detector includes a planar multilayer
core having a two-dimensional array of photo-sensitive
cells. An enclosure comprises first and second shells con-
nected together using a rail configured to be secured to at
least one of the first and second shells. The rail is attached
to at least one of the shells using screws.

20 Claims, 20 Drawing Sheets

(56)                    References Cited

U.S. PATENT DOCUMENTS

| | | | |
|---|---|---|---|
| 8,324,584 | B2 | 12/2012 | Sumi |
| 8,642,967 | B2 | 2/2014 | Iwakiri et al. |
| 8,680,475 | B2 | 3/2014 | Konkle |
| 9,322,934 | B2 | 4/2016 | Ogura et al. |
| 2007/0085015 | A1 | 4/2007 | Castleberry |
| 2011/0024633 | A1 | 2/2011 | Aoyagi et al. |
| 2013/0043400 | A1 | 2/2013 | Nakatsugawa et al. |
| 2013/0264461 | A1 | 10/2013 | Okada et al. |
| 2013/0292577 | A1 | 11/2013 | Lee et al. |
| 2014/0027636 | A1 | 1/2014 | Watano |
| 2015/0253441 | A1 | 9/2015 | Horiuchi et al. |
| 2015/0309194 | A1 | 10/2015 | Sumi et al. |
| 2017/0025761 | A1* | 1/2017 | Kim ..................... A61B 6/4452 |
| 2017/0294247 | A1 | 10/2017 | MacLaughlin |
| 2018/0263580 | A1 | 9/2018 | Kim |
| 2019/0196032 | A1* | 6/2019 | Horiuchi ................ G01T 1/244 |
| 2019/0216415 | A1* | 7/2019 | Wojcik ................ A61B 6/4283 |
| 2020/0121273 | A1* | 4/2020 | Bogumil .................. A61B 6/54 |

FOREIGN PATENT DOCUMENTS

| | | | |
|---|---|---|---|
| JP | 5381327 | B2 | 10/2013 |
| WO | 2015/111983 | A1 | 7/2015 |
| WO | 2016/028003 | A1 | 2/2016 |

* cited by examiner

RADIOGRAPHIC DETECTOR

This application is a continuation-in-part of U.S. patent application Ser. No. 17/627,705, filed Jan. 17, 2022, in the name of Bogumil et al., and entitled RADIOGRAPHIC DETECTOR, which is a 371 U.S. National Phase filing of PCT Application PCT/US2020/045592, filed on Aug. 10, 2020 which claims priority to U.S. Patent Application Ser. No. 62/885,423, filed Aug. 12, 2019, in the name of Bogumil et al., and entitled RADIOGRAPHIC DETECTOR, which is hereby incorporated by reference herein in its entirety.

BACKGROUND OF THE INVENTION

The subject matter disclosed herein relates to digital radiographic (DR) detectors used with x-ray systems in medical imaging facilities.

Portable digital radiographic detectors have been widely deployed to improve diagnostic radiographic imaging productivity, image quality and ease of use. In particular, mobile or bedside radiographic imaging is conducted in locations such as intensive care units so that the patient does not need to be transported from their critical care environment. This type of imaging procedure is best served by a portable detector that is light weight and durable to improve ease of use and reliability.

Current digital radiographic detectors typically include an amorphous silicon TFT/photo diode image sensor array that is fabricated on glass using semiconductor processes that are similar to those used for flat panel displays. A scintillator is combined with the image sensor array along with required electronics for signal readout and processing onto an internal core plate which is contained within a durable housing to create the portable DR detector.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g., an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photosensor cells 22 and, for clarity of description, it will be assumed that the rows extend horizontally, and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g., a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. A portion or all of the acquisition control and image processing unit 34 functions may reside in the detector 40 in an on-board processing system 36 which may include a processor and electronic memory to control operations of the DR detector 40 as described herein, including control of circuits 28, 30, and 32, by use of programmed instructions, and to store and process image data similar to the functions of standalone acquisition control and image processing system 34. The image processing system may perform image acquisition and image disposition functions as described herein. The image processing system 36 may control image transmission and image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e., it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g., a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure, or core, comprising a flexible photosensor array portion 22 of the DR detector 300. The housing portion 314 of the DR detector 300 may include a continuous, rigid or flexible, x-ray opaque material or, as used synonymously herein, a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the core in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber, carbon fiber embedded plastic, polymeric, elastomeric and other plastic based material.

With reference to FIG. 4, there is illustrated in schematic form an exemplary cross-section view along section 4-4 of the exemplary embodiment of the DR detector 300 (FIG. 3). For spatial reference purposes, one major surface, or side, of the DR detector 400 may be referred to as the top side 451 and a second major surface, or side, of the DR detector 400 may be referred to as the bottom side 452, as used herein. The core layers, or sheets, may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the core layered structure to allow adjustable curvature of the core layered structure and/or to provide shock absorption. The flexible layer 406 may be selected to provide an amount of flexible support for both the top cover 312 and the scintillator 404, and may comprise a foam rubber type of material. The layers just described comprising the multilayer core structure each may generally be formed in a rectangular shape and defined by edges arranged orthogonally and disposed in parallel with an interior side of the edges 318 of the housing 314, as described in reference to FIG. 3.

A substrate layer 420 may be disposed under the imaging array 402, such as a rigid glass layer, in one embodiment, or flexible substrate comprising polyimide or carbon fiber upon which the array of photosensors 402 may be formed to allow adjustable curvature of the array, and may comprise another layer of the core layered structure. Under the substrate layer 420 a radio-opaque shield layer 418, such as lead, may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, the bias circuit 32, and processing system 36 (all shown in FIG. 1) may be formed adjacent the imaging array 402 or, as shown, may be disposed below frame support member 416 in the form of integrated circuits (ICs) electrically connected to printed circuit boards (PCBs) 424, 425. The imaging array 402 may be electrically connected to the readout electronics 424 (ICs) over a flexible connector 428 which may comprise a plurality of flexible, sealed conductors known as chip-on-film (CoF) connectors.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the core layered structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Recently, processes have been developed that enable fabrication of the image sensor array onto durable thin substrates such as polyimide. This highly durable substrate enables the use of alternative housing components that are lighter in weight since the need for glass protection is reduced.

The discussion above is merely provided for general background information and is not intended to be used as an aid in determining the scope of the claimed subject matter.

BRIEF DESCRIPTION OF THE INVENTION

A digital radiographic detector includes a planar multi-layer core having a two-dimensional array of photo-sensitive cells. An enclosure comprises first and second shells connected together using a rail configured to be secured to at least one of the first and second shells. The rail is attached to at least one of the shells using screws.

In one embodiment, a digital radiographic detector is enclosed by two covers each having sidewall portions. The detector is disposed between the two covers. A plurality of rails extend along the sidewall portions of the covers, and a plurality of screws each extend through at least one of the covers and into the rail for securing the cover to the rail.

In one embodiment, an enclosure for a digital radiographic detector has a first shell and a second shell configured to be fastened together to form the enclosure. The shells each have a sidewall portion with a corresponding height. A plurality of linear rigid rails each extend along one of the sidewall portions and are secured to the sidewall portions using screws.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
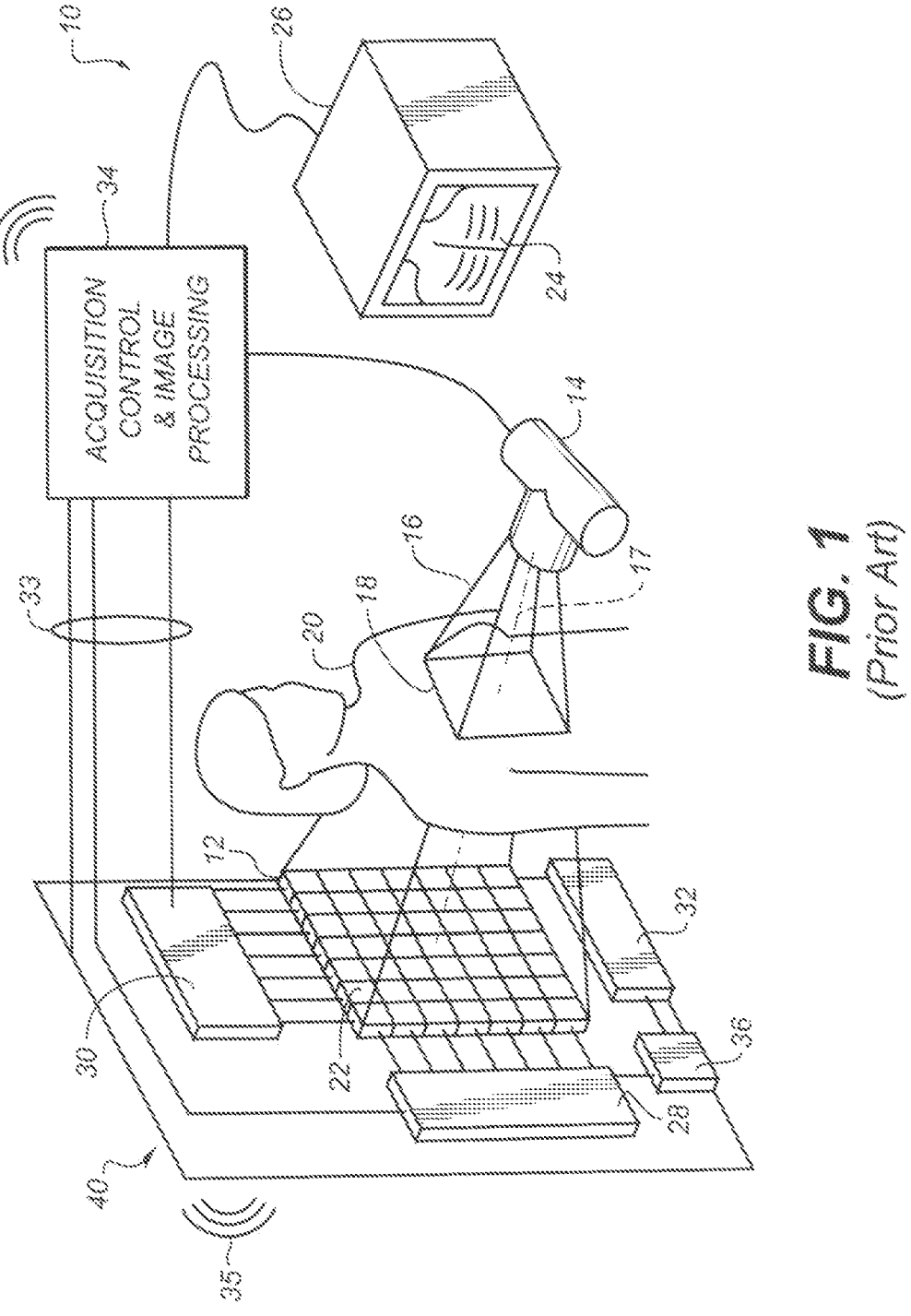
FIG. 1 is a schematic perspective view of an exemplary x-ray system.
Figure 2:
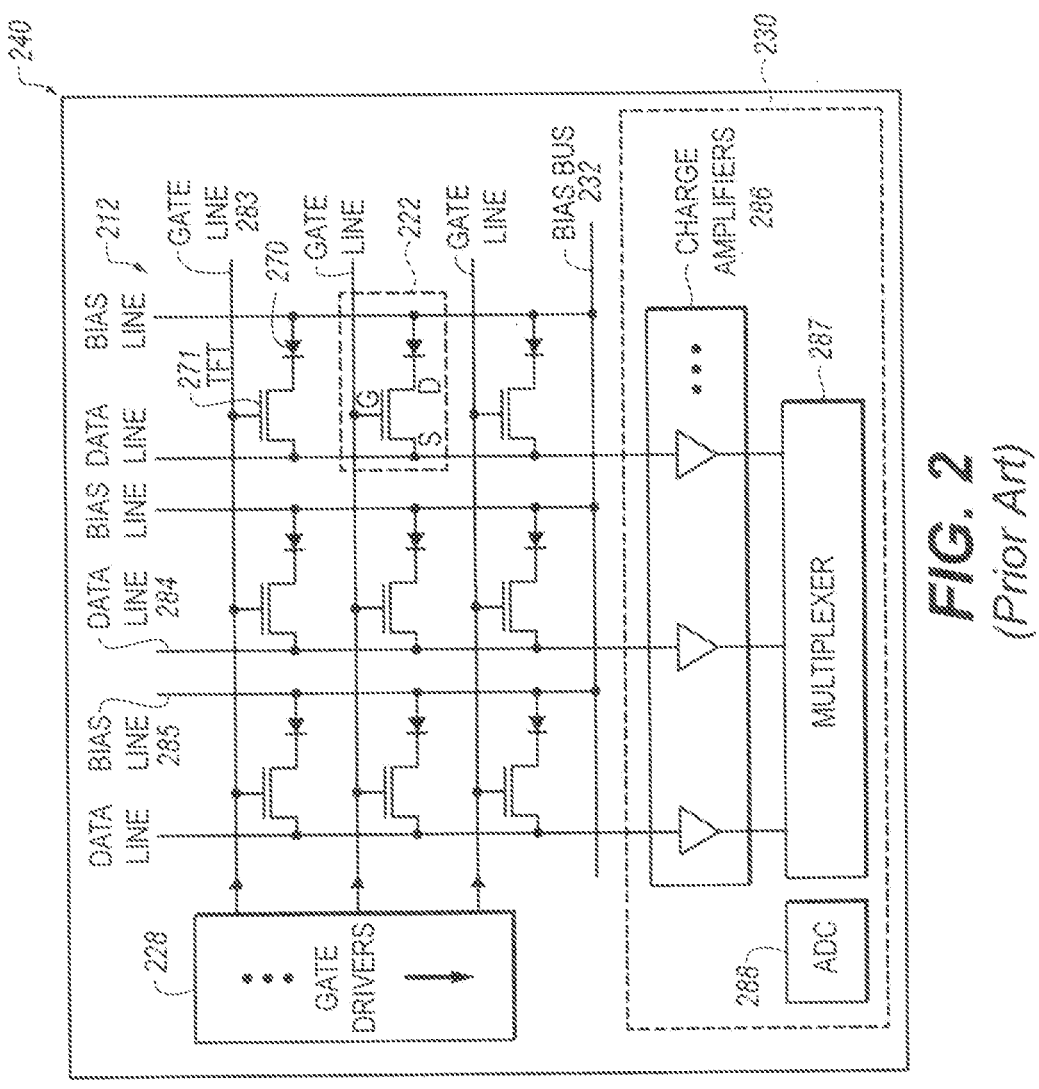
FIG. 2 is a schematic diagram of a photosensor array in a radiographic detector.
Figure 3:
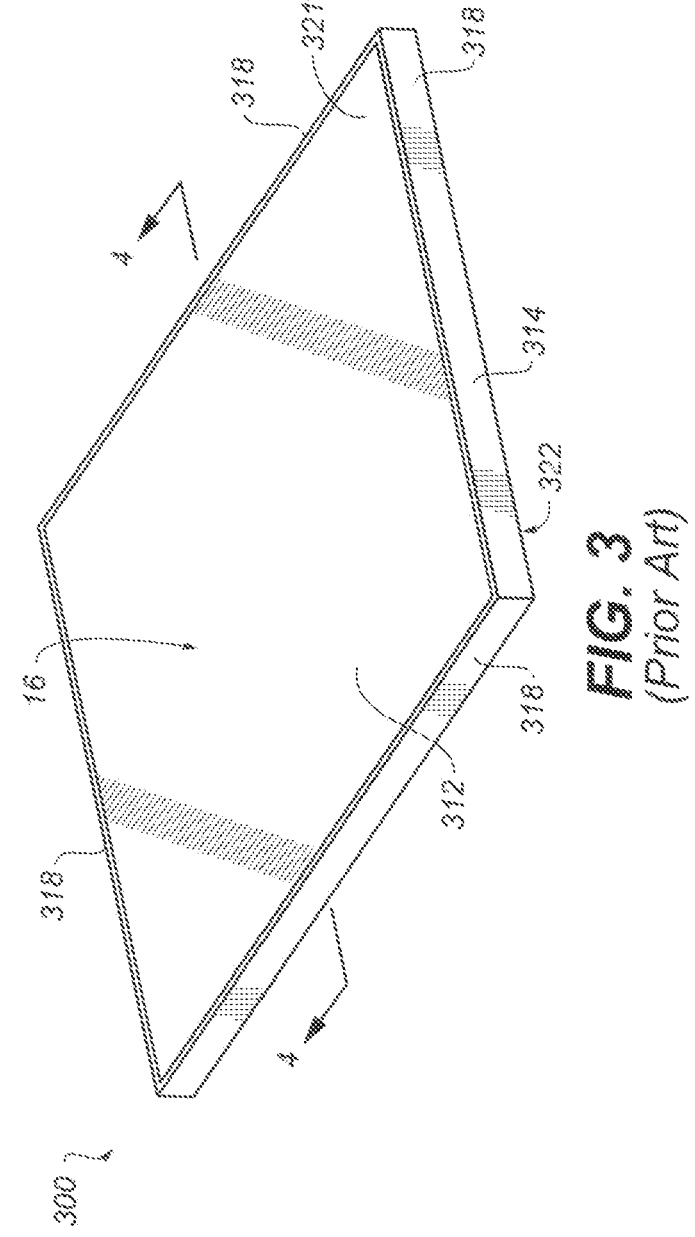
FIG. 3 is a perspective diagram of an exemplary DR detector.
Figure 4:
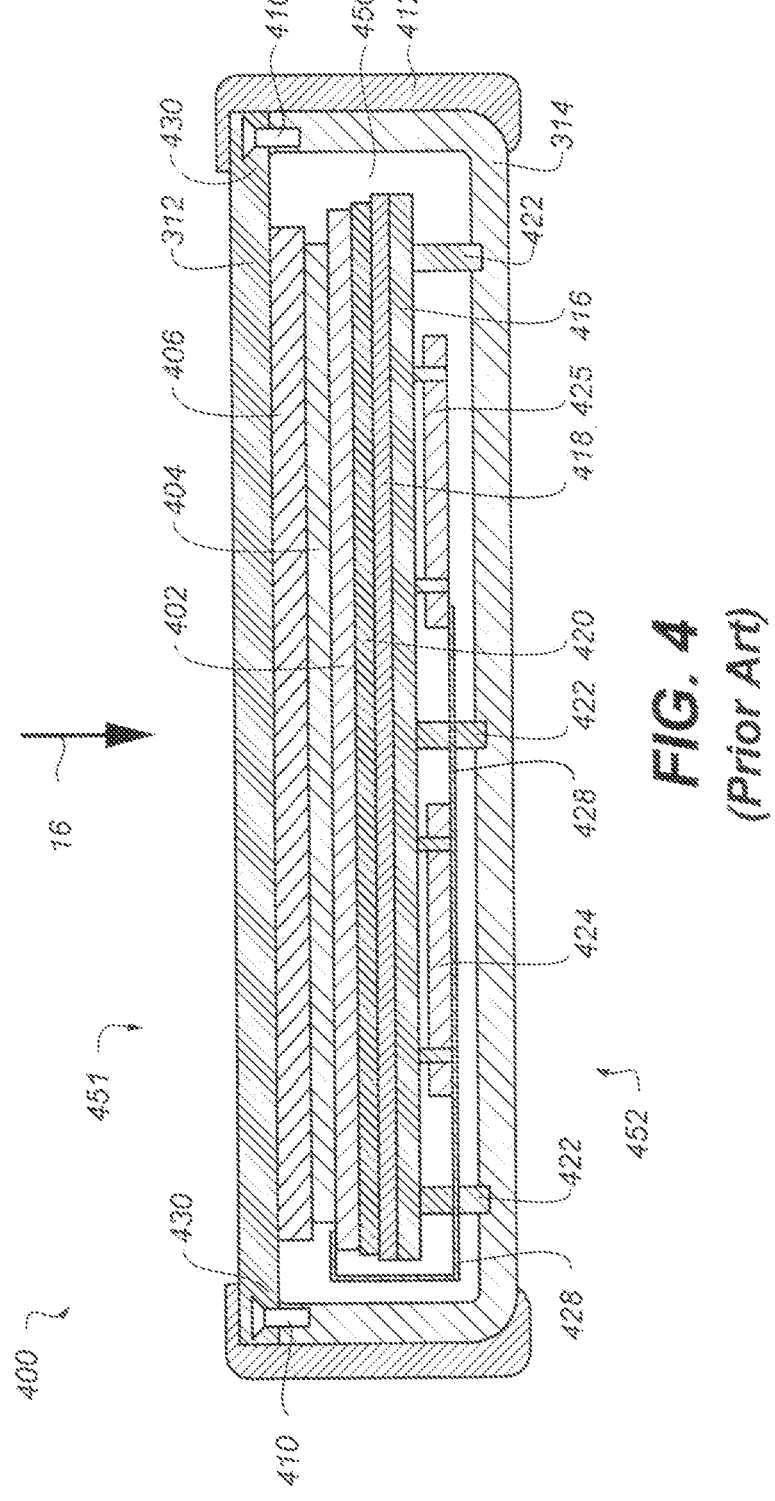
FIG. 4 is a cross section diagram of an exemplary DR detector.
Figure 5A:
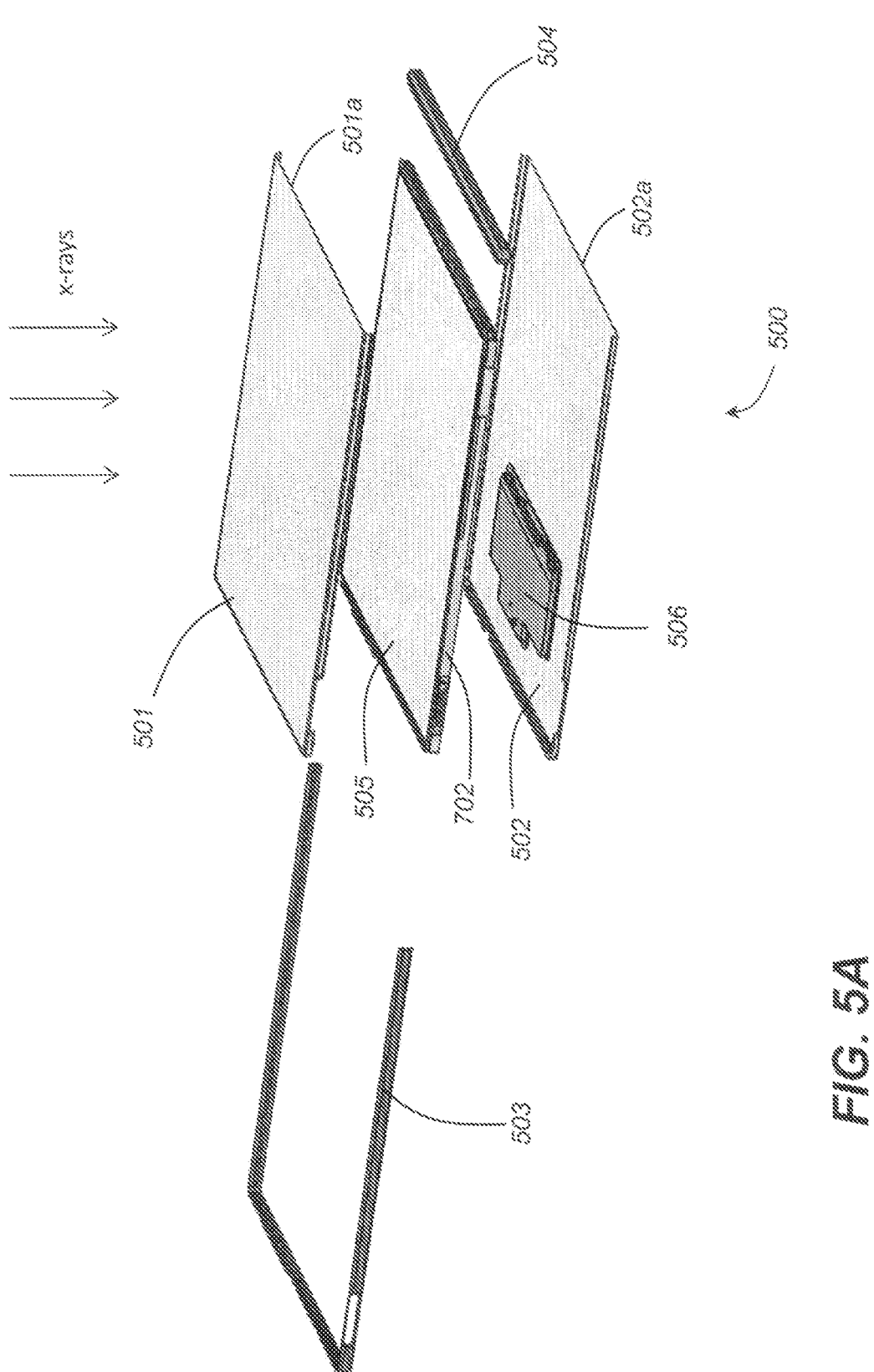
FIG. 5A is an exploded view of an exemplary DR detector assembly.

Referring to FIG. 5A, an exploded view of components of one embodiment of an inventive assembly for a DR detector 500 includes an upper shell 501 secured to a lower shell 502 using a U-shaped, or three-sided, bumper 503. The bumper 503 engages flanged edges (FIG. 7A) of the upper shell 501 and the lower shell 502 to secure them together. Adhesive may also be used between the flanged edges and on an inside surface of the bumper 503. When joined together, the upper shell 501 and the lower shell 502 leave an opening along a width of the shells because upper and lower shell edges 501a, 502a, respectively, are not flanged, or folded, and so do not contact each other. The upper and lower shells 501, 502, enclose a multilayer core 505 which includes a two dimensional array of photosensors, a scintillator, a support substrate and supporting electronics for reading out radiographic image data captured by the photosensors, which multilayer core 505 has been described herein. The upper and lower shells 501, 502, may be made from carbon fiber or similar material. As shown in FIG. 5A, the multilayer core may be secured in a core foam base 702. The opening along the width of the shells is closed by positioning an end cap 504 therein. Power is supplied to the DR detector by a battery placed in a battery compartment 506 formed in the lower shell 502. A battery compartment 506 is positioned in the lower shell 502 by forming a concave recess in an exterior bottom surface thereof. The term "shell" may be used herein interchangeably with the term "cover".

Figure 5B:
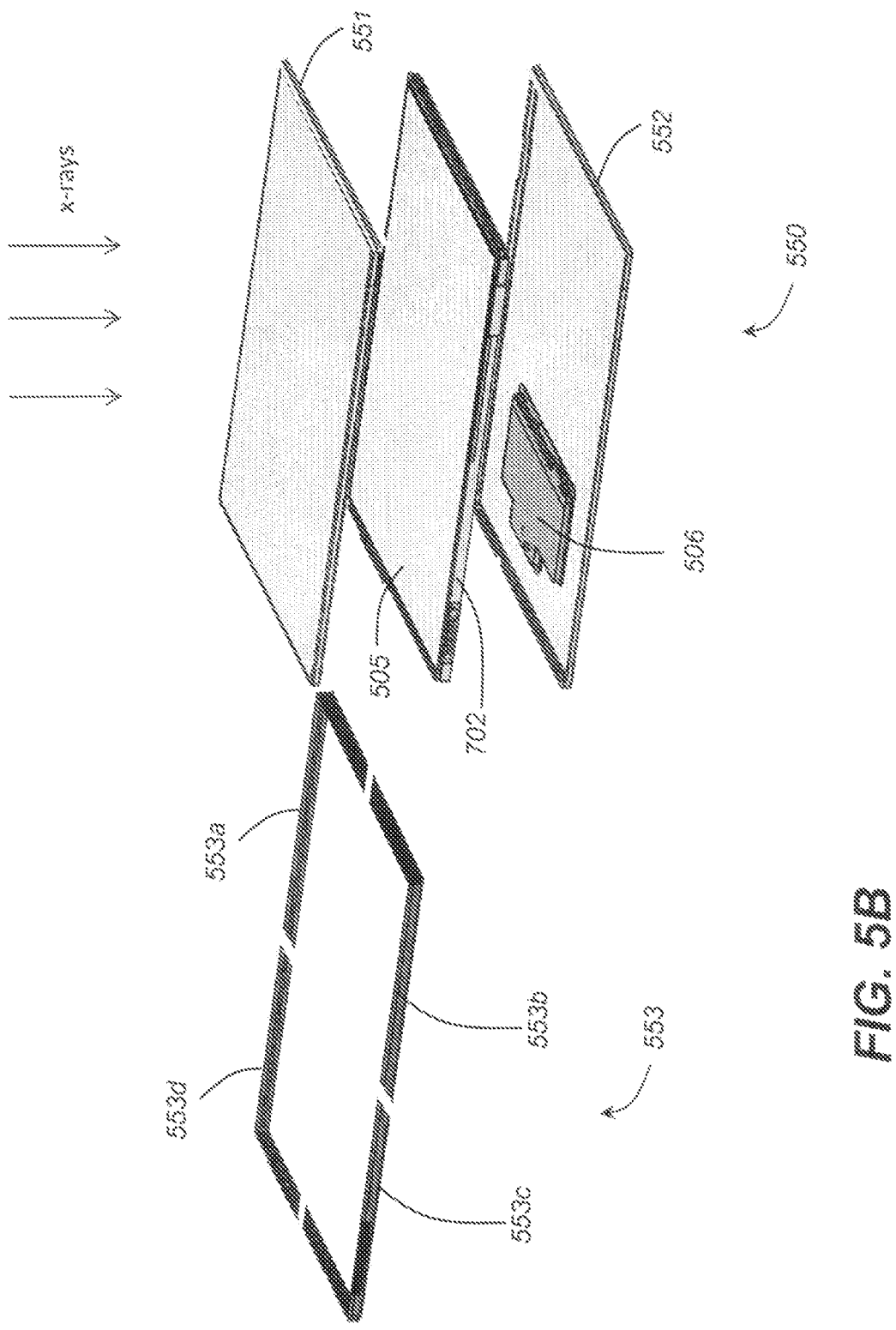
FIG. 5B is an exploded view of another exemplary DR detector assembly.

Referring to FIG. 5B, an exploded view of components of another embodiment of an inventive assembly for a DR detector 550 includes an upper shell 551 secured to a lower shell 552. All four edges of the upper and lower shells 551, 552, include flanged edges. A sectioned bumper 553, which, in one embodiment, includes a plurality of right-angled sections 553a-553d, engages the flanged edges of the top and bottom shells 551, 552, when the shells 551, 552, are positioned together. Adhesive may be optionally used between an inside surface of the sectioned bumper 553 and the flanged edges 551b, 552b (FIG. 7B), and/or between the inside surface of the sectioned bumper 553 and the top and bottom shells 551, 552. When joined together as described herein with reference to FIGS. 7B-7D, the upper shell 551 and the lower shell 552 sealingly enclose an interior volume 450 of the DR detector 550, which includes the multilayer core 505 having a two dimensional array of photosensors, a scintillator, a support substrate and supporting electronics for reading out radiographic image data captured by the photosensors. The upper and lower shells 551, 552, may be made from carbon fiber or similar material. As shown in FIG. 5B, the multilayer core 505 may be cushioned within the sealed shells 551, 552, using a foam 702. Power is supplied to the DR detector 550 by a battery placed in a battery compartment 506 formed in the lower shell 552.

Figure 5C:
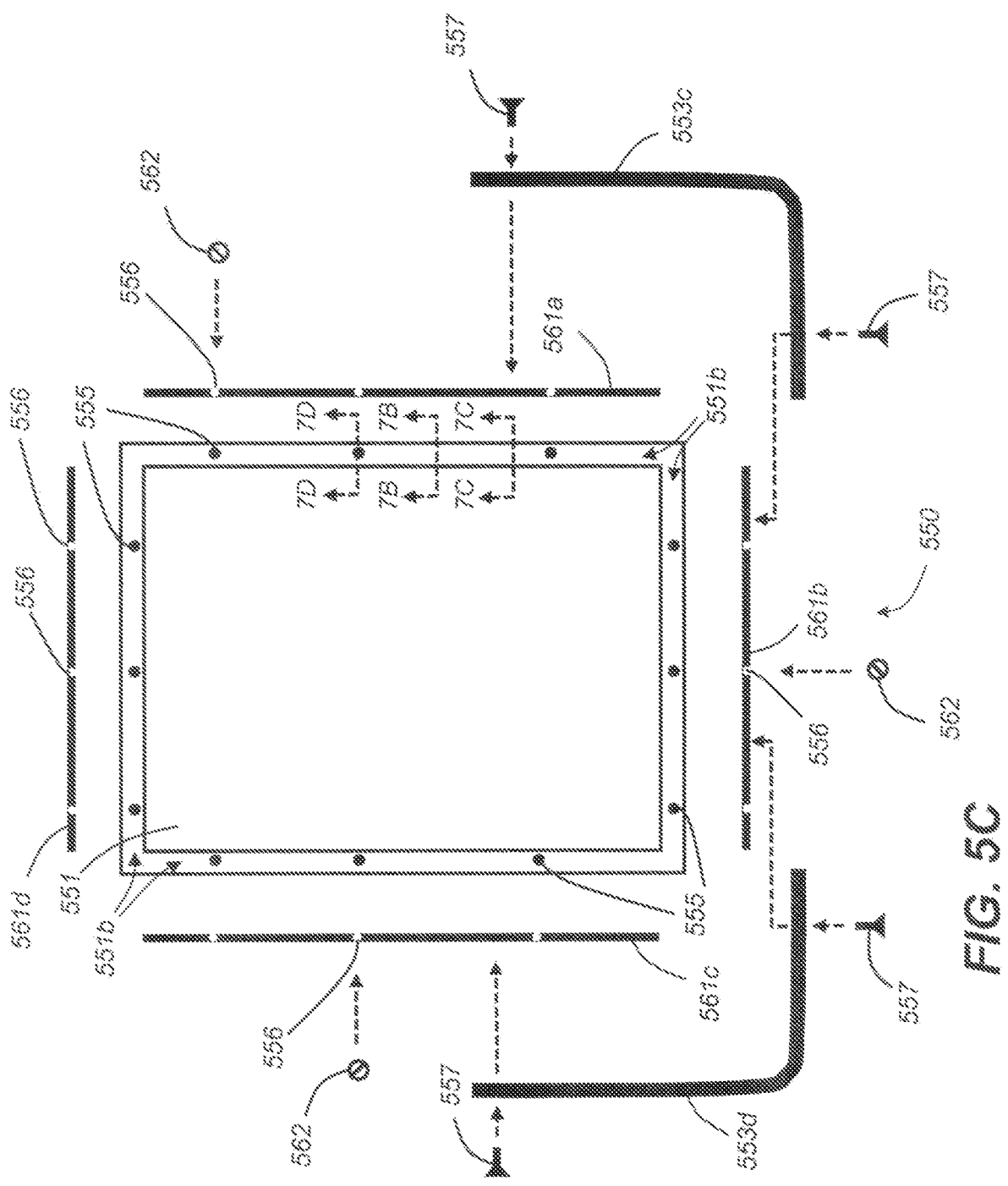
FIG. 5C is a top view of the exemplary DR detector assembly of FIG. 5B.

FIG. 5C is a schematic top view of the DR detector 550 showing the top shell 551 with flanged edges 551b having screw holes 555 in each of the four flanged edges 551b, which holes 555 may be threaded or not. Similar corresponding screw holes 558 (FIG. 7D) are formed in the flanged edges 552b of the bottom shell 552 and are aligned with the screw holes 555 (bottom shell not visible in FIG. 5C). Four linear rigid rails 561a-d, such as made from aluminum, for example, each having a plurality of threaded holes 556, are each positioned below one of the flanged edges 552b of the bottom shell 552 (FIGS. 7B-D). The holes 556 in the rails 561a-d are each aligned with corresponding holes 555, 558, in each of the flanged edges 551b, 552b, respectively. The top and bottom shells 551, 552, are joined together using screws 562 (FIG. 7D) passing through the holes 556, 558, in the top and bottom flanged edges 551b, 552b, respectively, and into the screw holes 556 of the rails 561a-d (FIG. 7D). The four bumper sections 553a-d may also be joined to the flanged edges 551b, 552b, using screws 557 that pass through openings 560 in the bumpers 553a-d (FIG. 7C) and engage corresponding threaded holes 559 (FIG. 7C) in the rails 561a-d. FIG. 5C illustrates in exemplary fashion the positioning and fastening of only two 553c, 553d, of the four bumpers 553a-d, which are all similarly attached.

Figure 6:
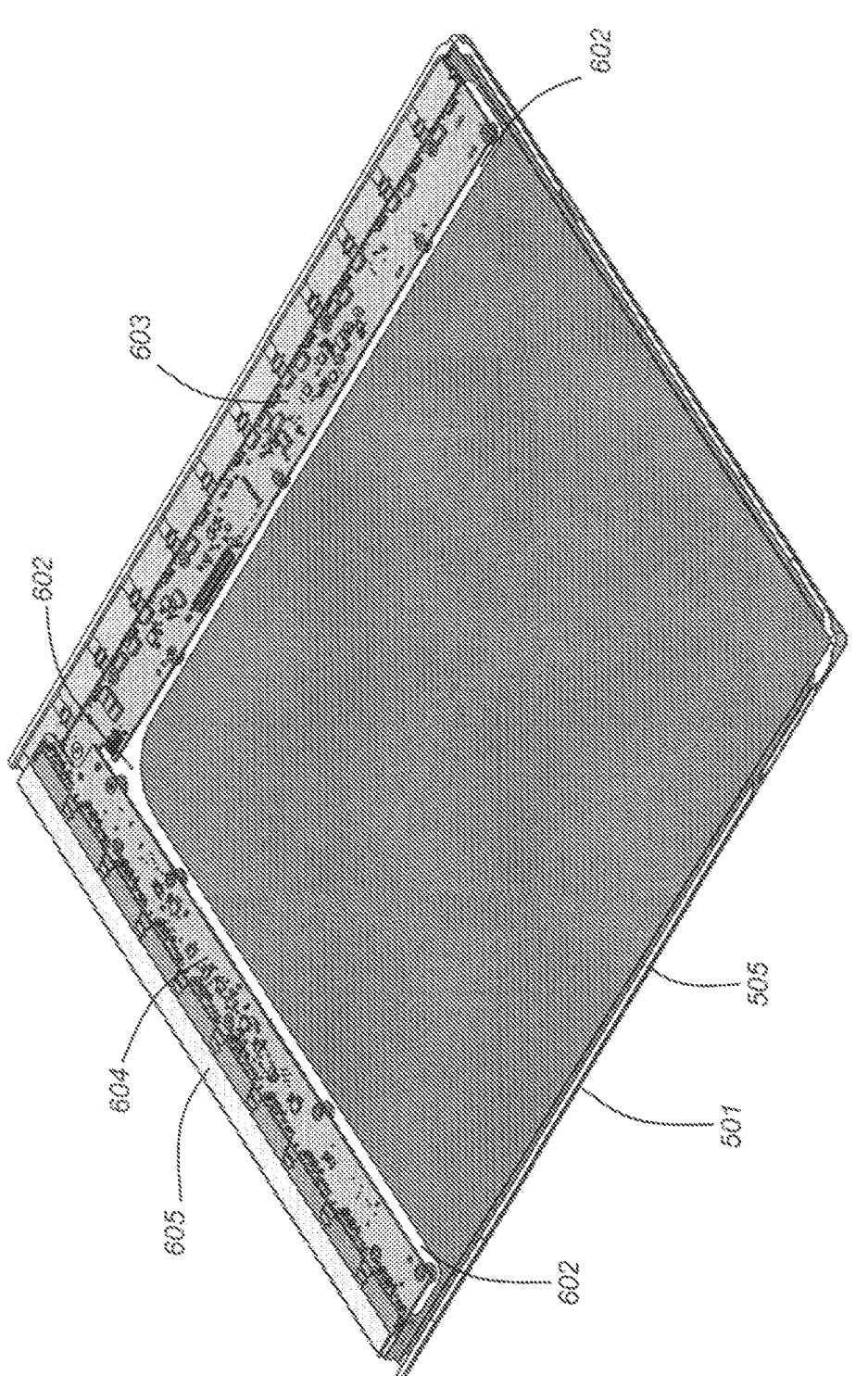
FIG. 6 is a perspective view of the upper shell having component layers laminated to the upper shell, shown upside down.

With reference to FIG. 6, a perspective view of the upper shell 501 is shown with the multilayer core 505 and additional components attached thereto. In one embodiment, an L-shaped grounding plate 602 is attached with adhesive either to a lead sheet, if a lead sheet 1003 (FIG. 12) is used; or, in another embodiment, the L-shaped grounding plate 602 is attached with adhesive to a stiffening member with adhesive, if a stiffening member 1302 (FIG. 14) is used; or, in another embodiment, the L-shaped grounding plate 602 is attached with adhesive directly to the multilayer core 505 (FIG. 12) if neither a stiffening member 1302 nor a lead sheet 1003 is used. The grounding plate 602 extends along two perpendicular peripheral edges of the DR detector 500, and may be made from aluminum or another suitable conductor. Gate driver integrated circuitry 603 is electrically attached to the grounding plate 602 along one edge thereof and read out integrated circuits (ROICS) 604 are electrically attached thereto along an adjacent perpendicular edge of the L-shaped grounding plate 602. A thermally conductive pad 605 is attached to, and is thermally coupled to, the ROICS 604. The end cap 504, when positioned in the open end of the joined shells 501, 502, thermally engages the thermally conductive pad 605 to act as a thermal sink for heat generated by ROICS 604.

Figure 7A:
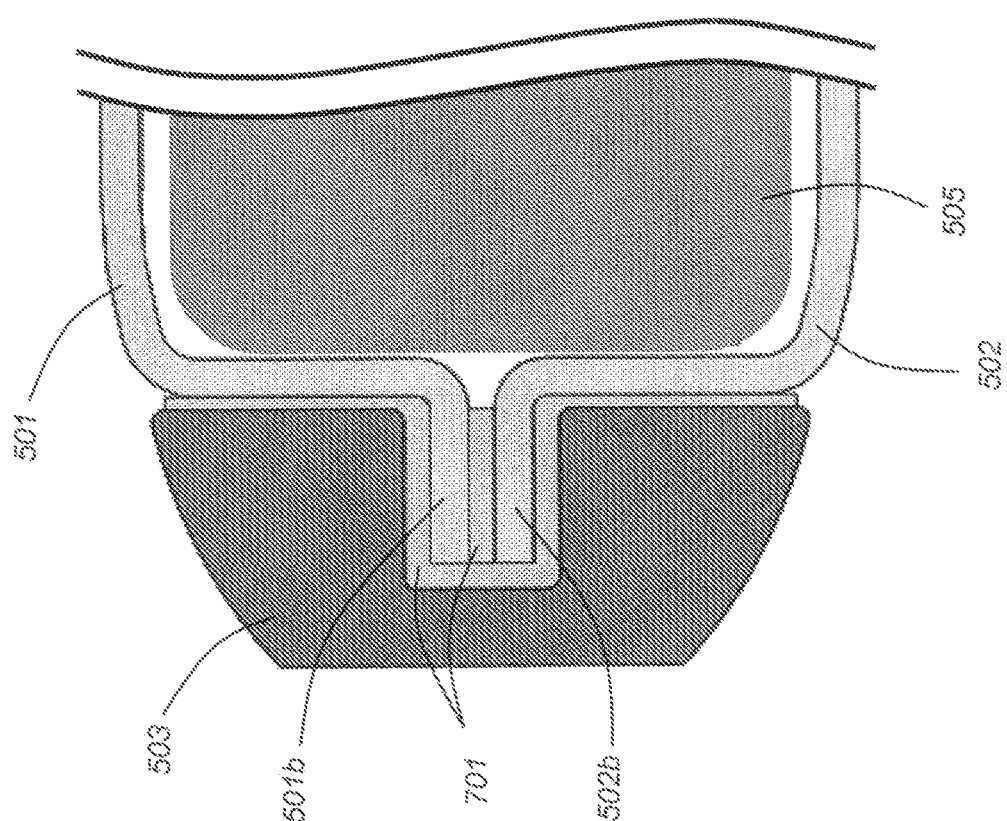
FIG. 7A illustrates a side edge cross section of a DR detector with interlocking bumper design.
Figure 7B:
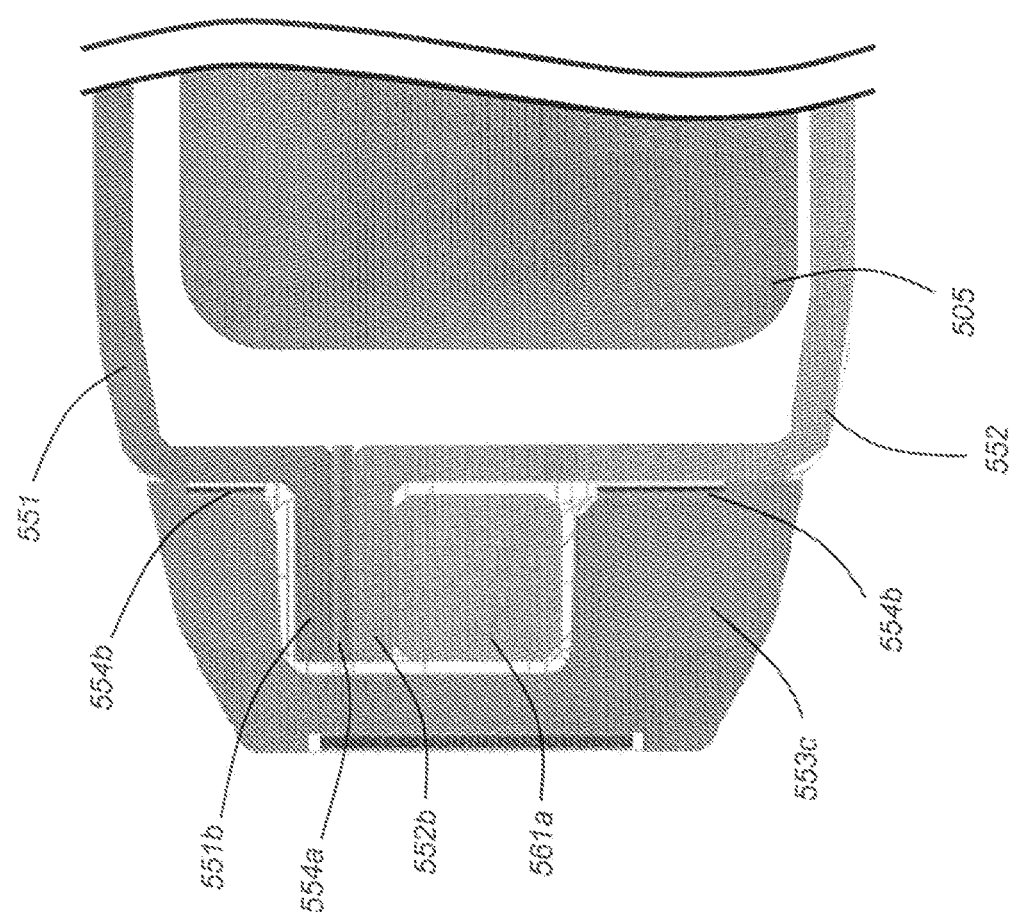
FIG. 7B illustrates a side edge cross section of another DR detector with flanged edges and rails.
Figure 7C:
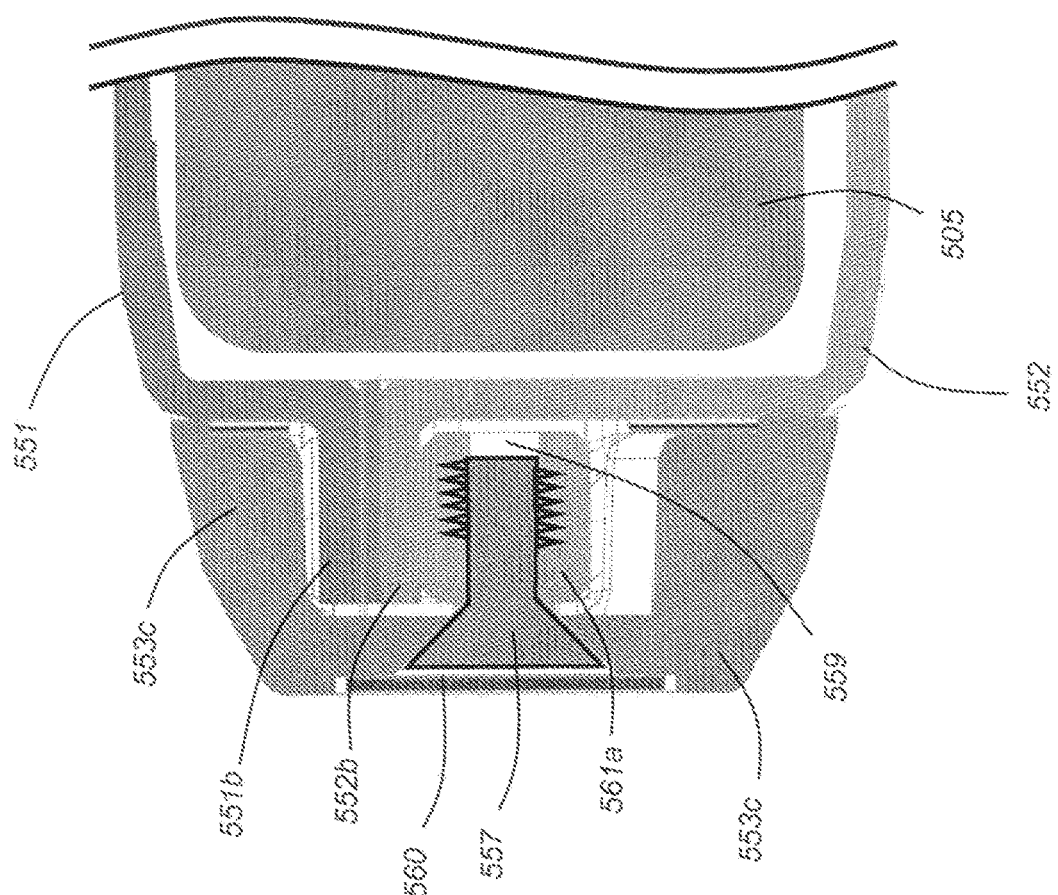
FIG. 7C illustrates another side edge cross section of the DR detector of FIG. 7B with bumper-rail connectors.
Figure 7D:
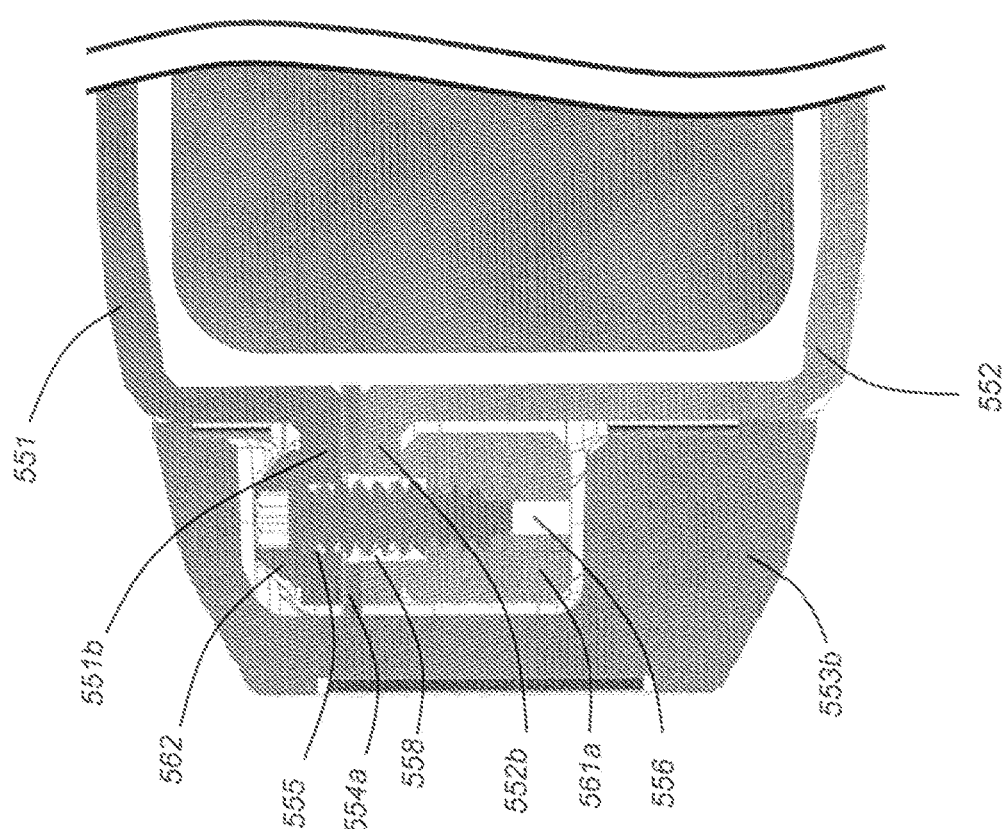
FIG. 7D illustrates another side edge cross section of the DR detector of FIG. 7B with flanged edge-rail connectors.

FIG. 7A illustrates a cross-section view of one edge of DR detector 500, of FIG. 5A, showing the engagement of bumper 503 to flange edge 501b of the upper shell 501 and to flanged edge 502b of the lower shell 502. The vertical sidewall portions of upper and lower shells 501, 502, respectively, in the perspective of FIG. 7A, bend and extend horizontally into bumper 503 to form flanged edges 501b, 502b, respectively. The bumper 503 secures together both the upper and lower shells, 501, 502, respectively, by compressive force against flanged edges 501b, 502b, and, in addition, adhesive 701 is disposed between upper and lower flanged edges 501b, 502b, between the bumper 503 and the upper and lower flanged edges 501b, 502b, and between the bumper 503 and the upper and lower shells 501, 502. As will be described herein, the multilayer core 505 is embedded in a core foam base 702 disposed in the interior area of DR detector 500. The bumper 503 may be made of an elastomeric material, plastic, rubber, or other suitable impact tolerant material, to absorb shock but should be suitably rigid to hold together the upper and lower shells 501, 502.

FIG. 7B illustrates a cross-section view of one edge of DR detector 550 labeled as 7B-7B in FIG. 5C showing the engagement of bumper 553c to flange edges 551b, 552b, of the upper and lower shells 551, 552. The bumper section 553c engages flanged edges 551b, 552b, which may have a sealing gasket 554a disposed therebetween, which may be made from a polyurethane foam, for example. The bumper section 553c also engages sidewalls of the upper and lower shells 551, 552, which may have a similar sealing gasket 554b disposed therebetween. As described herein, the multilayer core 505 may be embedded in a core foam base and is disposed in the interior volume 560 of DR detector 550. The bumper sections 553a-d may be made of an elastomeric material, plastic, rubber, or other suitable impact tolerant material, to absorb shock but should be suitably rigid to securely engage the upper and lower flanged edges 551b, 552b. Rail 561a is shown positioned underneath and abutting lower flanged edge 552b.

FIG. 7C illustrates a cross-section view of one edge of DR detector 550 labeled as 7C-7C in FIG. 5C showing the engagement of bumper 553c to flange edges 551b, 552b, of the upper and lower shells 551, 552. Threaded screw 557 is shown passing through an opening 560 in bumper section 553c and engaging threaded screw hole 559 of rail 561a, which is positioned underneath and abutting lower flanged edge 552b.

FIG. 7D illustrates a cross-section view of one edge of DR detector 550 labeled as 7D-7D in FIG. 5C showing the engagement of bumper 553b to flange edges 551b, 552b, of the upper and lower shells 551, 552. Threaded screw 562 is shown passing through screw hole 555 in flanged edge 551b, through an opening in sealing gasket 554a, through screw hole 558 in flanged edge 552b and engaging threaded screw hole 556 of rail 561a, which is positioned underneath and abutting lower flanged edge 552b. The FIGS. 7B-7D illustrate in an exemplary fashion how the top and bottom shells are secured together along one flanged edge of the DR detector 550, using exemplary screws and rail 561a. The other three flanged edges are similarly configured using rails 561b-d.

Figure 7E:
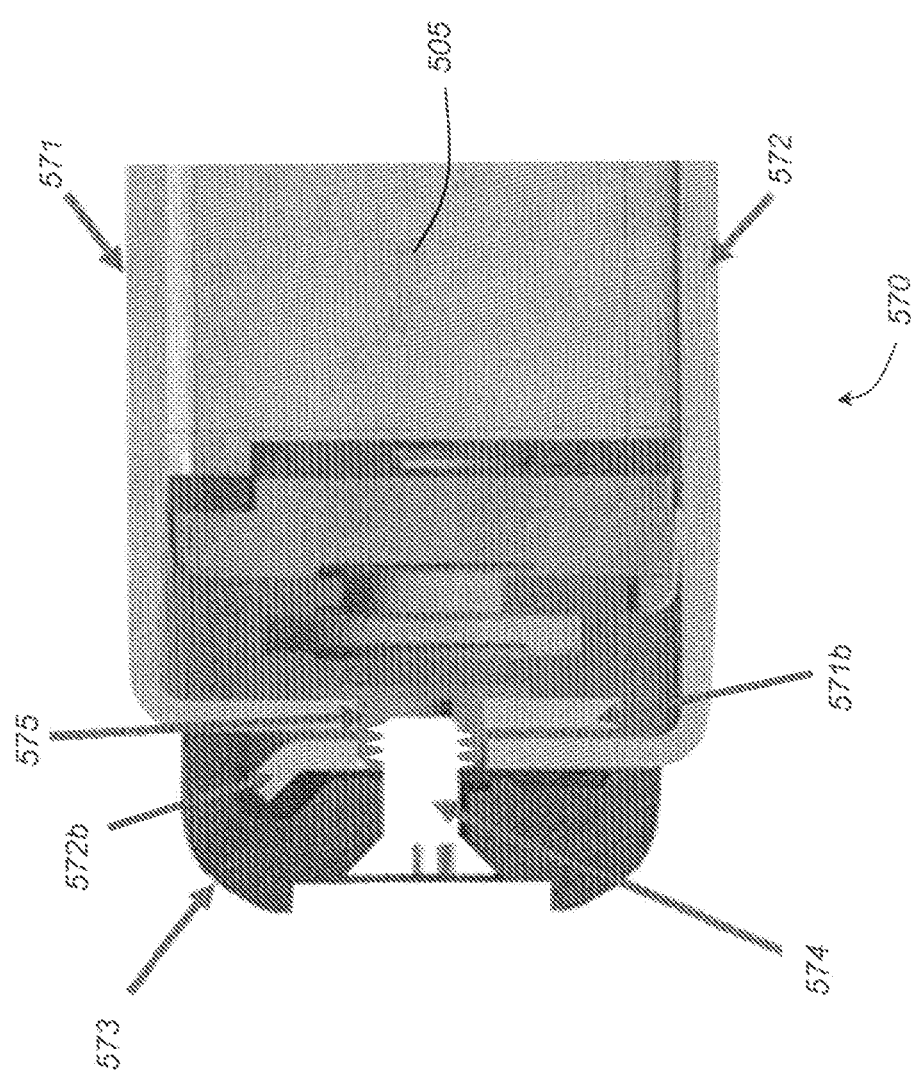
FIG. 7E illustrates a side edge cross section of an alternative DR detector with connected overlapping sidewalls.

FIG. 7E illustrates a cross-section view of one edge of an alternative DR detector 570, showing the engagement of bumper 573 to overlapping sidewalls 571b, 572b, of the upper and lower shells 571, 572, respectively. The overlapping vertical sidewall portions 571b, 572b, of upper and lower shells 571, 572, respectively, in the perspective of FIG. 7E, bend and extend vertically in an overlapping fashion. The vertical sidewall portions 571b, 572b, of upper and lower shells 571, 572, each have a plurality of openings aligned with each other, one of which is illustrated in FIG. 7E. The aligned openings in vertical sidewall portions 571b, 572b, allow positioning of a flanged nut 575 therethrough. The flange portion of flanged nut 575 abuts and is pressed against an inside surface of vertical sidewall portion 571b as the screw 574 is tightened while engaging flanged nut 575. Similarly, the screw 574 passes through an opening in bumper 573 that is aligned with the flanged nut 575 and secures the bumper 573 against vertical sidewall portion 572b. Thus, the bumper 573 is secured all around against the sidewall of DR detector 570 while the upper and lower shells 571, 572 are sealably fastened together. A sealant or gasket may be positioned between the overlapping portions of the vertical sidewall portions 571b, 572b.

Figure 8:
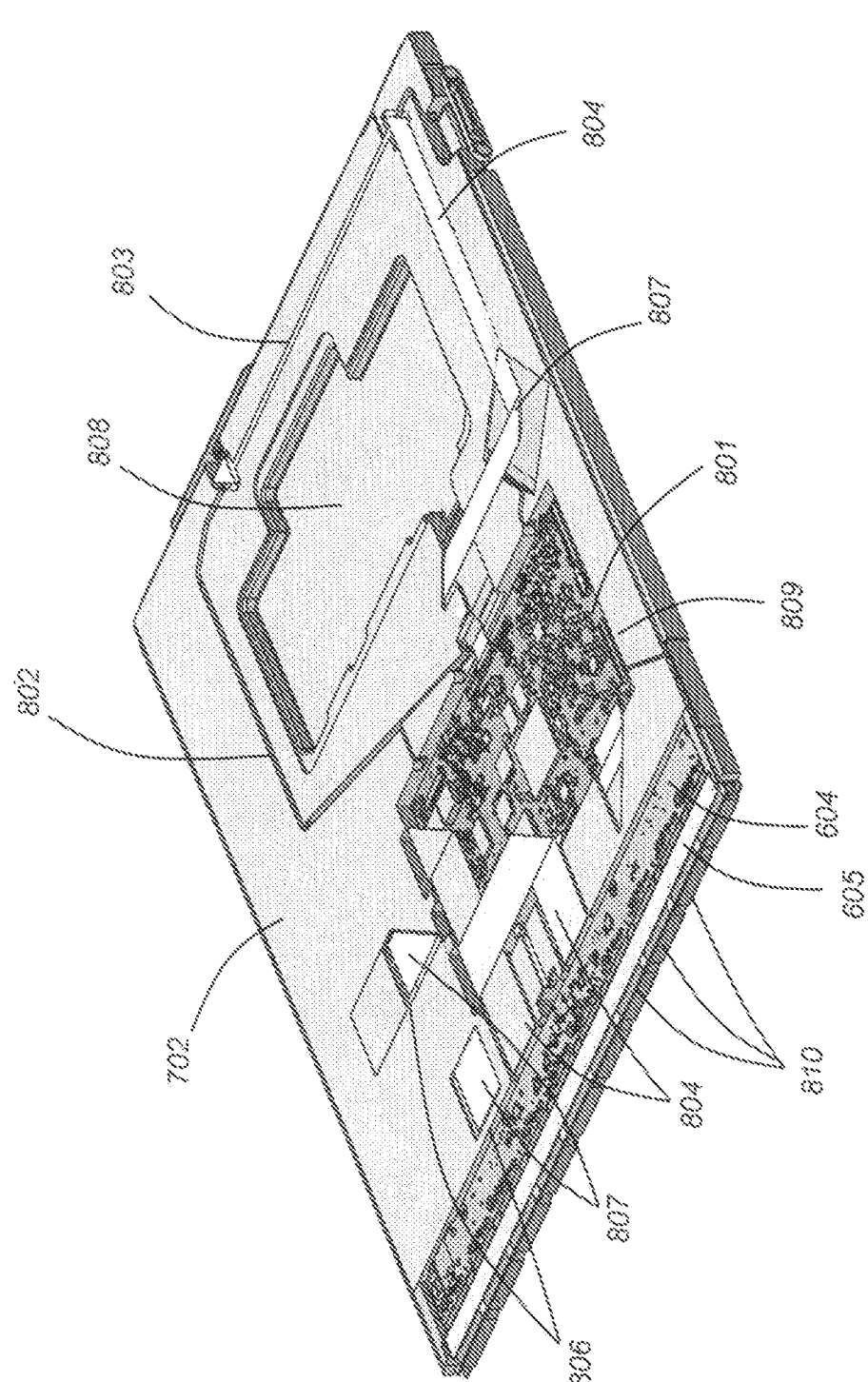
FIG. 8 is an internal detector assembly with foam core base populated with printed circuit board and related electronics.

FIG. 8 is a perspective view of the core foam base 702, and other internal electronic components of DR detector 500, which includes shaped recesses 806, cutouts 809, pockets 808, and wirelines 802 to receive components of DR detector 500, and which occupies a major volume of the interior of the DR detector 500 between upper and lower shells 501, 502. Recesses 806 may be used to provide space for folds 807 of the ribbon cables 804, which provide for data and electrical communication between ROICS 604 and the PCB main control circuitry 801 via chip-on-film connectors 810, among other communications; pockets 808 may be used for providing space for a battery, for example; wirelines 802 may each be used to press a wire 803 therein in order to secure the wire in position within DR detector 500. Components of the PCB main control circuitry 801 are positioned within the edges of a cutout 809.

Figure 9:
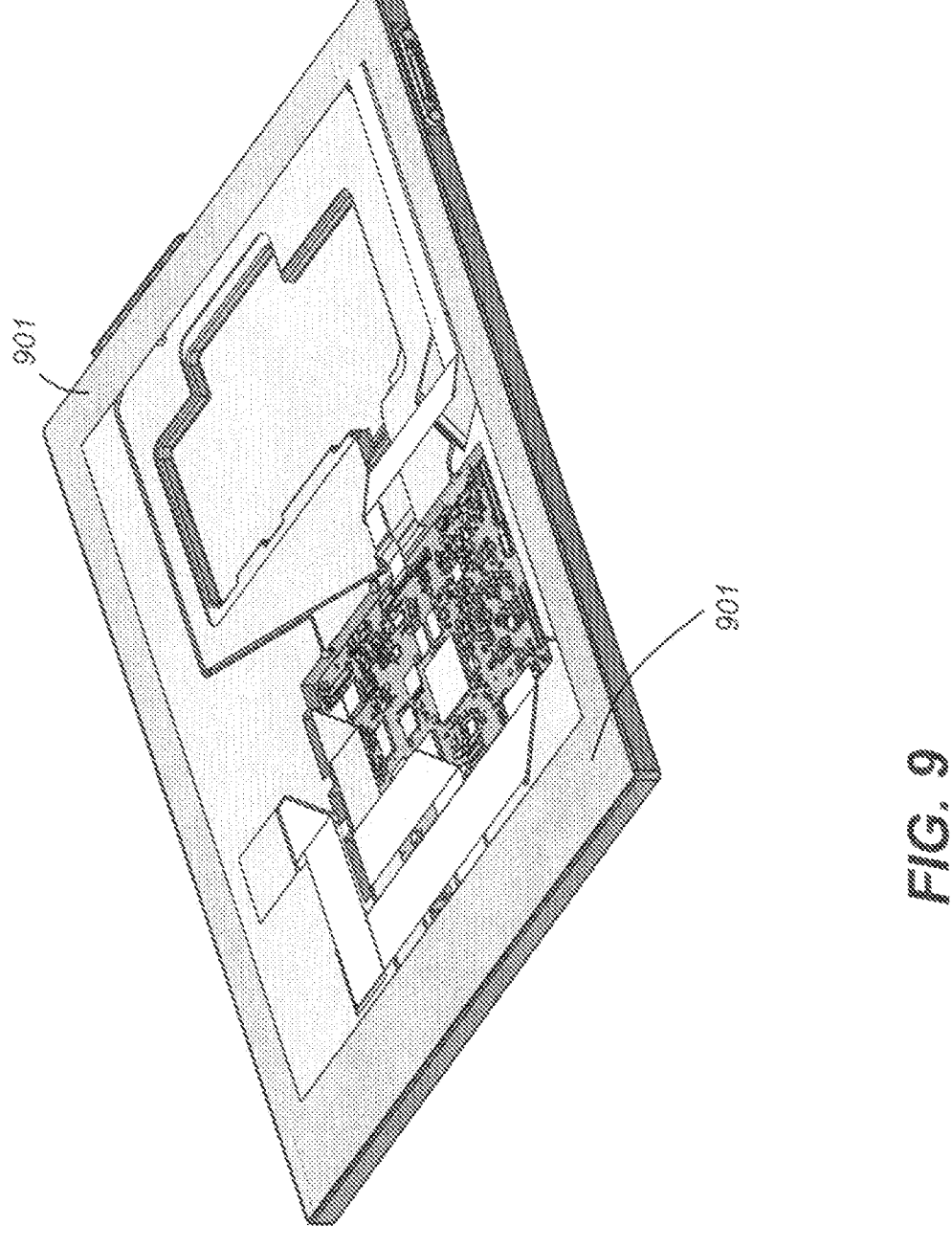
FIG. 9 shows a conformal adhesive release layer over portions of the internal detector assembly of FIG. 8.

FIG. 9 is a perspective view similar to FIG. 8 but with a conformal adhesive release layer, film, sheet, or tape, 901 place along a periphery of the assembly of FIG. 8. The release layer 901 covers the ROICS 604, chip-on-film connectors 810, and portion of the DR detector interior assembly. The release layer 901 prevents seeping or leaking adhesive from contacting portions of DR detector 500 that are covered by the release layer 901. Release layer 901 also serves as a sacrificial layer that may be peeled off when separating the upper and lower shells 501, 502, during a repair procedure. Release layer 901 also assists in separating the upper and lower shells 501, 502, for repair purposes by preventing excess adhesive or glue from contacting the upper shell 501.

Figure 10:
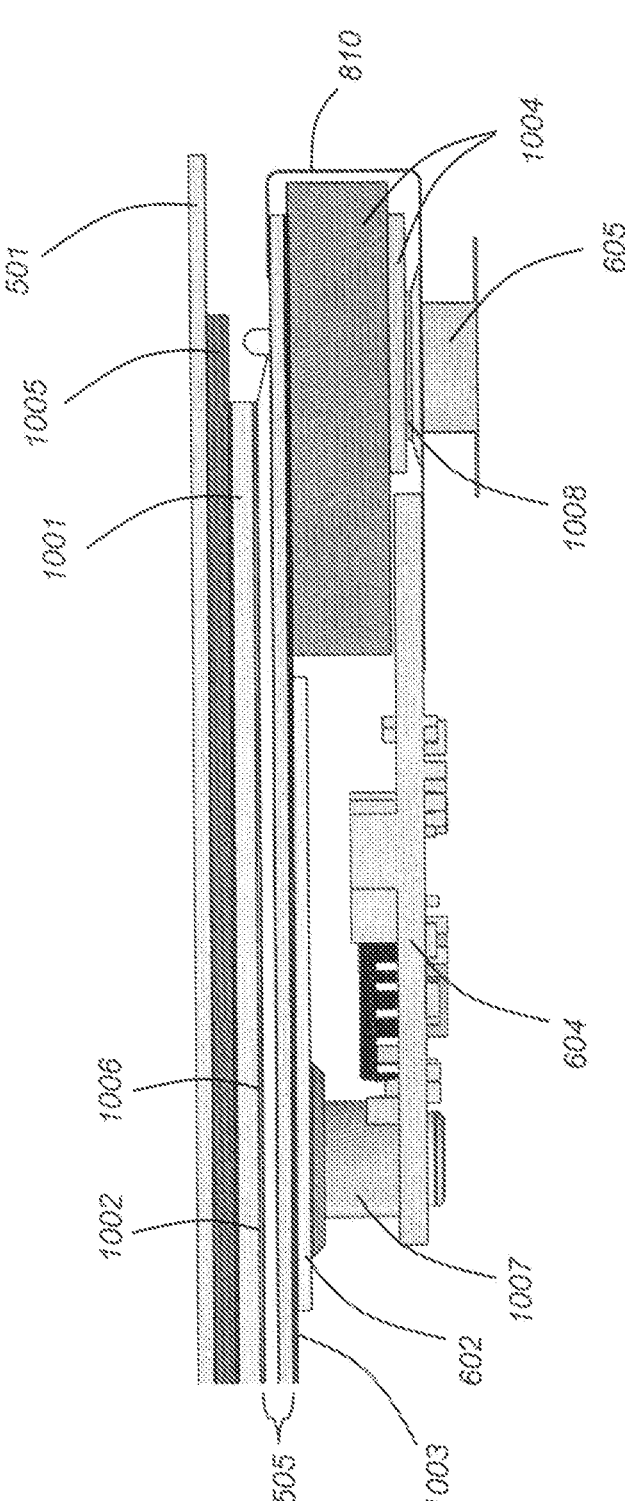
FIG. 10 shows a cross-section cut away portion of the multilayer sensor laminate structure.
Figure 11:
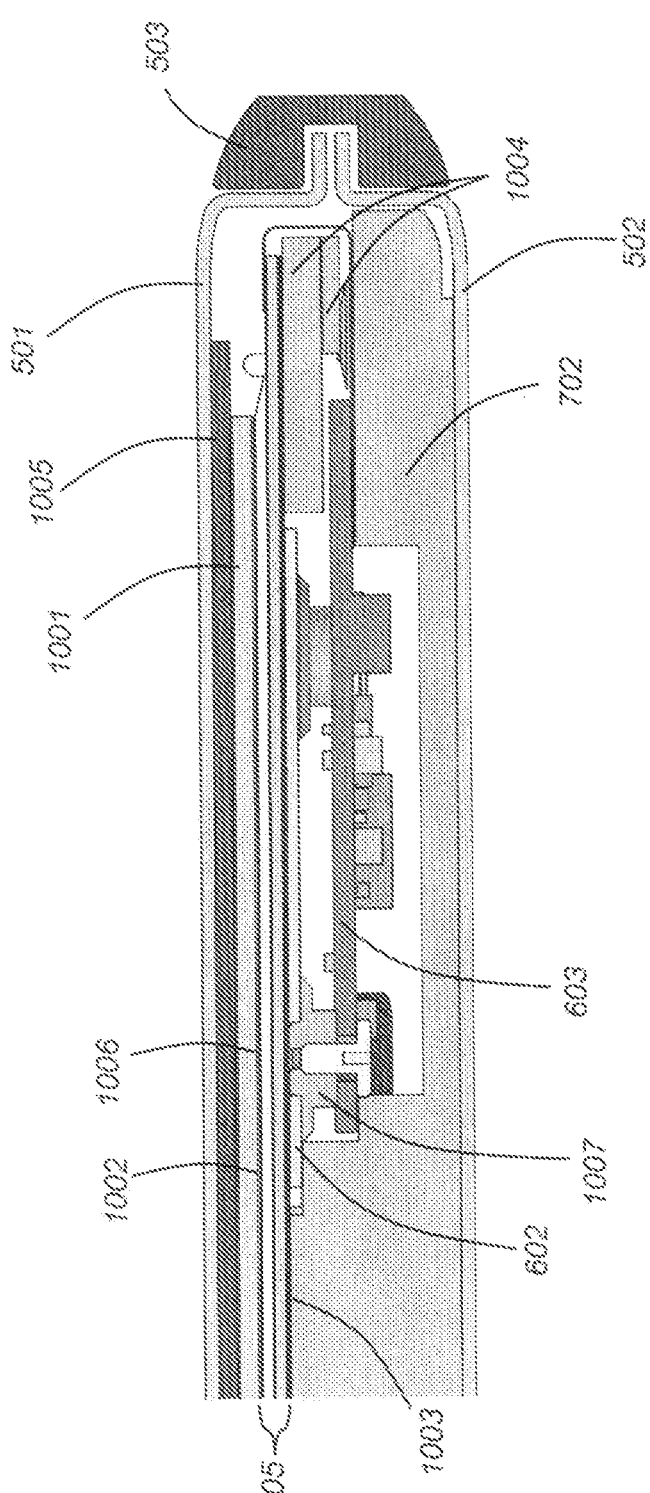
FIG. 11 shows a DR detector partial cross-section.

FIG. 10 is a cross-section cut away view of a portion of DR detector 500 without core foam base 702 to illustrate positioning of certain described components. FIG. 11 is a cross-section view near one edge of assembled DR detector 500 showing relative positioning of the components of FIG. 10 from a view perpendicular to the view of FIG. 10. Adhered to an interior surface of upper shell 501 is a carbon fiber stiffening member 1005 which strengthens upper shell 501 against distortion caused by weight placed thereon. In one embodiment, the upper shell 501 is manufactured to have a thicker structure of about 1.5 mm up to about 2 mm thickness, instead of adhering the stiffening member 1005 thereto. The other portions of upper shell 501, i.e., sidewall area proximate the flanged edges, and lower shell 502 may have half the thickness of the upper shell 501. A buffer layer (foam) 1001 is positioned below the stiffening member 1005. The multilayer core 505 is positioned below the buffer layer 1001, which includes a scintillator layer, photosensor layer, and a substrate, such as a polyimide substrate. An optional, very thin, mylar sheet 1002 and conductive grounding sheet 1006 may be positioned between the buffer layer 1001 and the multilayer core 505. If included, the mylar sheet 1002 may be adhered to the buffer layer 1001, with the conductive sheet 1006 below. An optional lead (Pb) layer 1003 may be positioned under the substrate layer of the multilayer core 505. The grounding plate 602 is placed below the optional lead (Pb) layer 1003, if the lead layer 1003 is used, otherwise against the substrate layer of the multilayer core 505. The ROICS 604 (FIG. 10) are attached to the ground plate 602 using posts 1007; the gate driver ICs 603 are similarly attached to the ground plate 602 using posts 1007. Foam supports 1004 may be positioned between the multilayer core 505 and the thermal pad 605 (FIG. 10). The thermal pad 605 is in thermal contact with a heat generating IC chip 1008 mounted on chip-on-film conductor 810. Chip-on-film conductor 810 is in electrical communication with both photosensor electronics in the multilayer core 505 and ROICS 604, and wraps around intermediate layers as shown in FIG. 10. The core foam base 702 (FIG. 11) supports portions of the assembly as shown including the ROICS 604 (core foam base 702 not shown in FIG. 10) and gate driver PCB 603 (FIG. 11).

Figure 12:
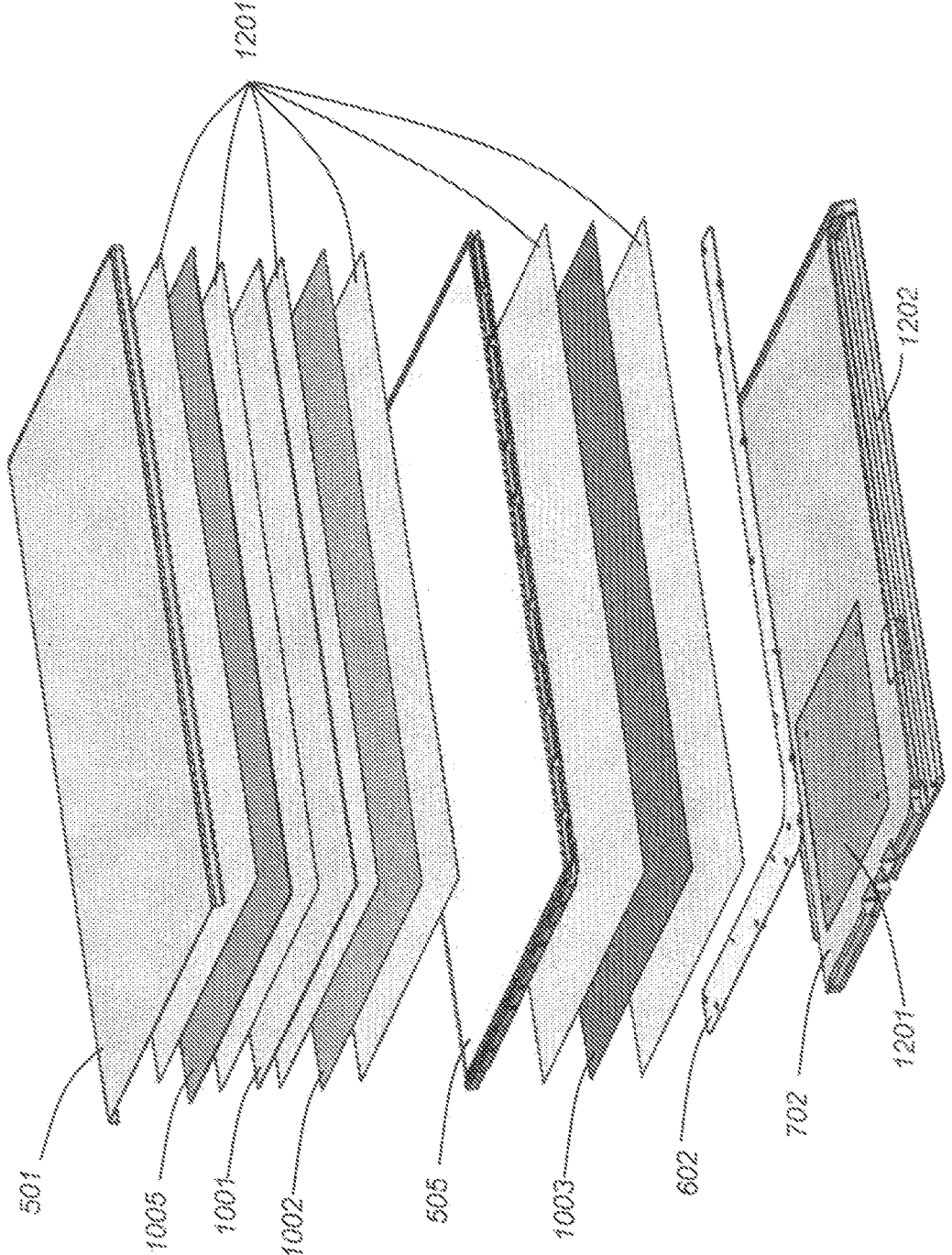
FIG. 12 shows an exploded view of the DR detector layers in more detail.

FIG. 12 shows several of the assembly components described herein in an exploded view. Each individual functional layer, enumerated along the left side of FIG. 12, is attached to an adjacent layer using adhesive 1201, except for the grounding plate 602 and core foam base 702. The upper shell 501 is adhered to carbon fiber stiffener 1005, which is adhered to buffer layer (foam) 1001, which is adhered to an optional, very thin conductive grounding sheet 1002, which is adhered to multi layer core 505, which is adhered to optional lead (Pb) sheet 1003, which is adhered to L-shaped grounding plate 602, which is supported by core foam base 702. As shown in FIG. 12, a carbon fiber bridge structure 1201 is positioned in a recess on the core foam base, to provide stiffness and to prevent excess loads on PCB main control 801 which is positioned directly underneath the carbon fiber bridge 1201, in the perspective of FIG. 12. The core foam base 702 is shaped along one edge 1202 to conform to, and support, gate driver integrated circuitry 603 (not shown) that is attached to an underside of ground plate 602, in the perspective of FIG. 12, as described in relation to FIG. 6.

Figure 13:
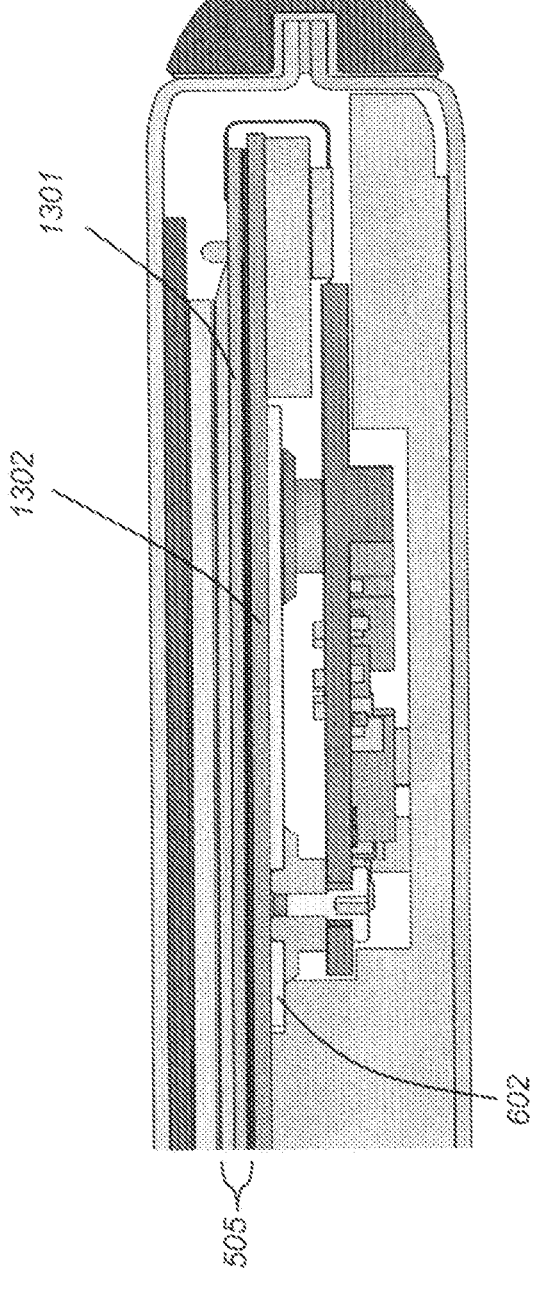
FIG. 13 shows a DR detector partial cross-section with an alternative glass substrate embodiment.
Figure 14:
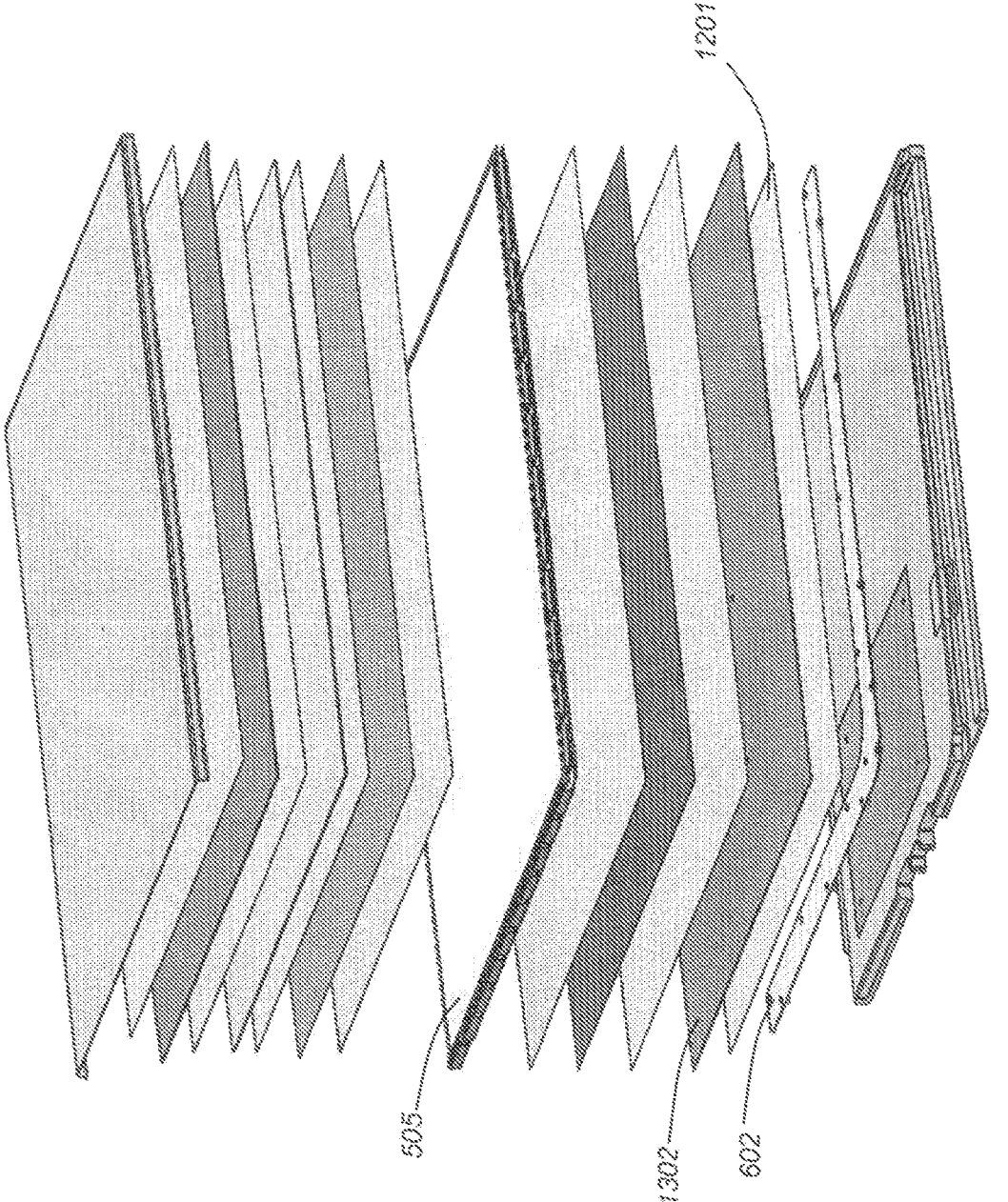
FIG. 14 shows an exploded view of the multilayer core with the additional stiffener layer for a glass substrate embodiment.

FIGS. 13 and 14 correspond substantially to FIGS. 11 and 12, respectively, and so enumeration of the same components will not be repeated in these figures. FIGS. 13 and 14 illustrate an optional use of a glass substrate 1301 as part of the multilayer core 505, rather than a polyimide substrate as shown in FIG. 11. Due to the glass substrate being more brittle than a polyimide substrate, an additional stiffening member 1302 is positioned beneath the multilayer core 505, however, this stiffening member 1302 may optionally be used with other substrates, such as polyimide. The stiffening member 1302 may be made from a carbon fiber composite, or other sturdy and stiff material. The stiffening member 1302 may also include a grounded, thin conductive layer thereon. The grounding plate 602 is then adhered to this stiffening member 1302.

As described herein, any foam layer components, including foam core base 702, buffer layer 1005, foam supports 1004, may be made from a lightweight low density foam. Examples of foam materials suitable for use as described herein include ULTEM™ foam, which is a polyetherimide thermoplastic foam, having a density of about 60 kg/m$^3$, that is thermoformable, manufactured by SABIC, based in Riyadh, Saudi Arabia. Another suitable foam is ZOTEK® foam which is a closed cell foam made from poly vinylidene fluoride, having a density of about 74 kg/m$^3$, that is thermoformable, manufactured by Zotefoams, in Walton, Kentucky, USA.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A digital radiographic detector comprising:
two covers configured to form an enclosure, each of the covers comprising sidewall portions;
radiographic image receptor pixels disposed between the covers;
a plurality of rails extending along the sidewall portions; and
a plurality of screws each extending through at least one of the covers and into the rail, for securing together the rail and said at least one of the covers.

2. The detector of claim 1, further comprising a plurality of bumpers extending along the sidewall portions and on an outside surface thereof, the bumpers each covering at least a part of the sidewall portions of each of the covers.

3. The detector of claim 2, wherein the plurality of rails are each disposed along the outside surface of the sidewall portions.

4. The detector of claim 2, wherein the two covers comprise a top cover and a bottom cover, the detector configured to capture a radiographic image when the top cover is facing a radiographic energy source.

5. The detector of claim 4, wherein the top and bottom covers each comprise a rectangular shape having flanged edges on each of four sides thereof.

6. The detector of claim 5, wherein the screws each extend through the flanged edges of both the top and bottom covers.

7. The detector of claim 5, wherein at least two of the bumpers overlap along one of the sidewall portions.

8. The detector of claim 2, wherein at least some of the bumpers comprise an L shape for extending around a corner of the detector.

9. The detector of claim 8, further comprising a flexible seal disposed between the flanged edges of the top and bottom covers.

10. The detector of claim 9, wherein the flexible seal comprises a gasket.

11. The detector of claim 1, wherein one of the two covers comprises a sidewall portion having a greater height than the sidewall portion of the other cover.

12. The detector of claim 1, wherein the rail comprises one of aluminum, magnesium, a polymer, carbon fiber, or steel.

13. An enclosure for a digital radiographic detector, the enclosure comprising:

a first shell and a second shell configured to be fastened together to form the enclosure, the first shell and the second shell each comprising a sidewall portion having a height;

a plurality of linear rigid rails each extending along one of the sidewall portions; and a plurality of screws each extending through at least one of the shells and into one of the rails.

14. The enclosure of claim 13, further comprising a plurality of bumpers extending along an outside surface of the sidewall portions of the top and bottom shells.

15. The enclosure of claim 14, wherein the sidewall portion of the first shell comprises a height greater than the sidewall portion of the second shell.

16. The enclosure of claim 15, wherein the plurality of rails are each disposed along an outside surface of the sidewall portion of the first shell.

17. The enclosure of claim 16, wherein the first and second shells each comprise a rectangular shape having flanged edges facing each other on each of four sides thereof.

18. The enclosure of claim 17, wherein the plurality of screws each extend through the flanged edges facing each other and into one of the rails.

19. The enclosure of claim 17, wherein the plurality of bumpers each comprise an L shape for extending around a corner of the enclosure.

20. The enclosure of claim 17, further comprising a gasket between the flanged edges facing each other.

\* \* \* \* \*